(12) United States Patent
Geist

(10) Patent No.: US 6,488,666 B1
(45) Date of Patent: Dec. 3, 2002

(54) APPARATUS FOR PREVENTING USED HYPODERMIC NEEDLE STICKS

(75) Inventor: Leroy D. Geist, Parker, CO (US)

(73) Assignee: Vital Signs, Inc., Totawa, NJ (US)

( * ) Notice: Subject to any disclaimer, the term of this patent is extended or adjusted under 35 U.S.C. 154(b) by 352 days.

(21) Appl. No.: 09/625,888

(22) Filed: Jul. 26, 2000

Related U.S. Application Data

(63) Continuation-in-part of application No. 09/577,022, filed on May 23, 2000, now abandoned.

(51) Int. Cl.[7] .................................................. A61M 5/00
(52) U.S. Cl. ........................ 604/263; 604/192; 604/264
(58) Field of Search .................. 604/263, 192, 604/198, 110, 164.08, 411, 533, 264; 206/366; 53/468

(56) References Cited

U.S. PATENT DOCUMENTS

| | | | | |
|---|---|---|---|---|
| 4,931,048 A | * | 6/1990 | Lopez .......................... | 604/110 |
| 5,135,489 A | * | 8/1992 | Jepson et al. ................ | 600/578 |
| 5,312,346 A | * | 5/1994 | Han ........................... | 206/365 |
| 5,347,078 A | * | 9/1994 | Eckels ......................... | 206/365 |
| 5,352,200 A | * | 10/1994 | Hammett et al. ............ | 604/110 |
| 5,451,213 A | * | 9/1995 | Teicher et al. .............. | 604/192 |
| 5,505,705 A | * | 4/1996 | Galpin et al. ................ | 128/919 |
| 5,643,219 A | * | 7/1997 | Burns .......................... | 604/192 |
| 5,718,689 A | * | 2/1998 | Stevenson ................... | 128/919 |
| 5,743,888 A | * | 4/1998 | Wilkes et al. ............... | 604/192 |
| 5,797,885 A | * | 8/1998 | Rubin ......................... | 604/192 |
| 6,036,671 A | * | 3/2000 | Frey ........................... | 206/364 |
| 6,059,758 A | * | 5/2000 | Padilla et al. ............... | 604/192 |
| 6,077,253 A | * | 6/2000 | Cosme ........................ | 128/919 |
| 6,213,996 B1 | * | 4/2001 | Jepson et al. ............... | 604/256 |

* cited by examiner

Primary Examiner—Teresa Walberg
Assistant Examiner—Vinod D. Patel
(74) Attorney, Agent, or Firm—R. Gale Rhodes, Jr.

(57) ABSTRACT

Apparatus for locking or latching a used hypodermic needle in a needle sheath; an adapter for locking to a needle sheath to entrap a hypodermic needle between the adapter and a needle sheath, a needle sheath for receiving a used hypodermic needle, and the combination of the adapter and the needle sheath. A kit including a syringe barrel, a syringe needle, an adapter and a needle sheath. Combination syringe needle and cantilever latching apparatus, such combination in further combination with a needle sheath and a further kit including such combinations and a syringe barrel.

51 Claims, 13 Drawing Sheets

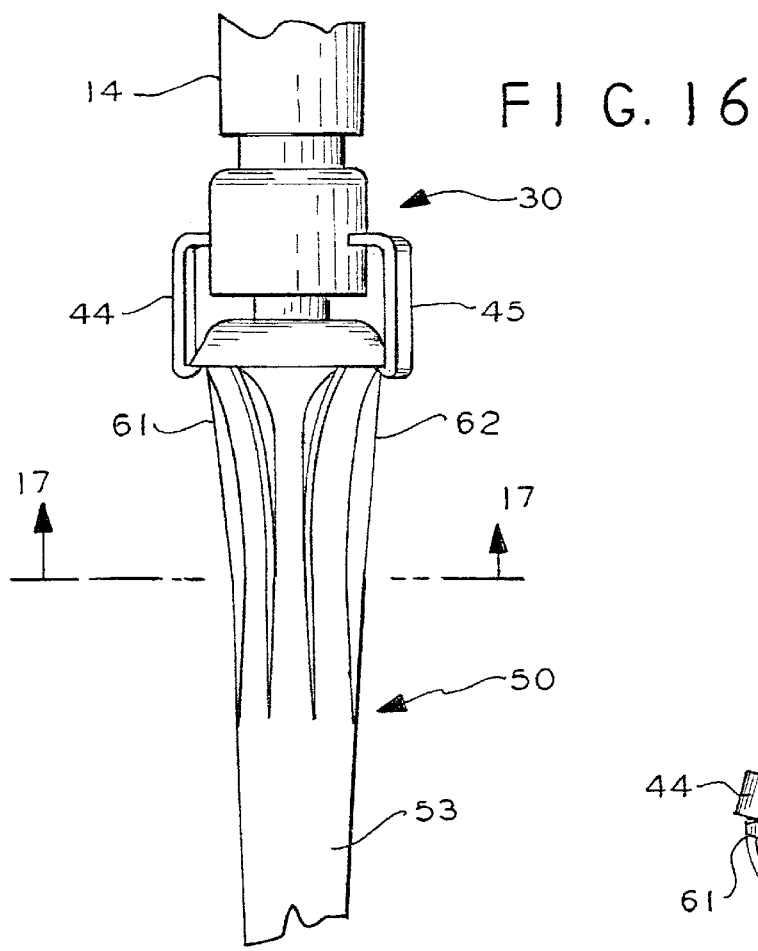
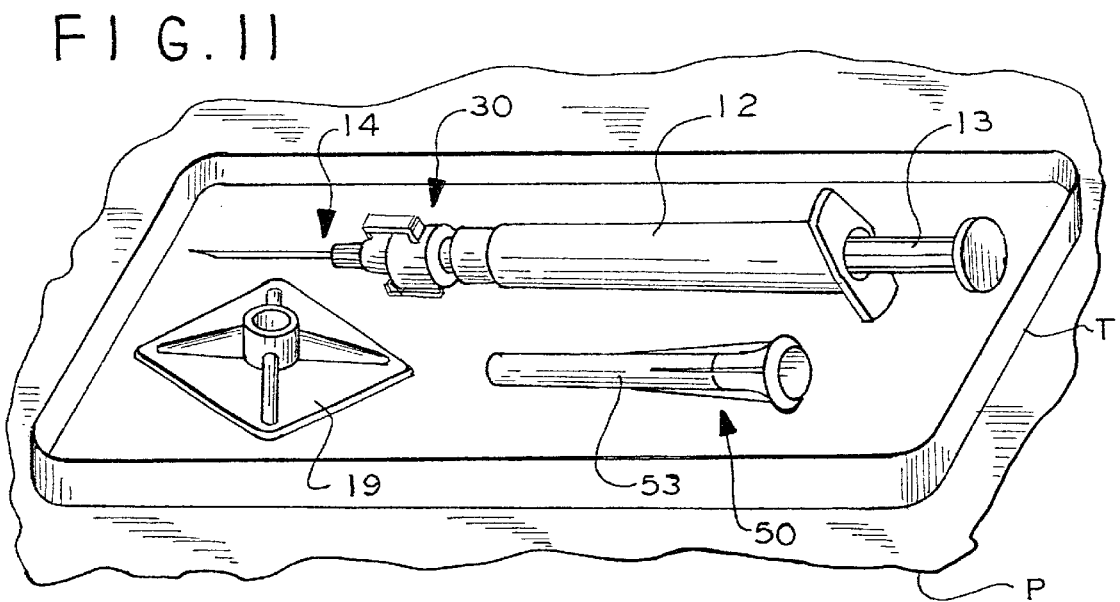

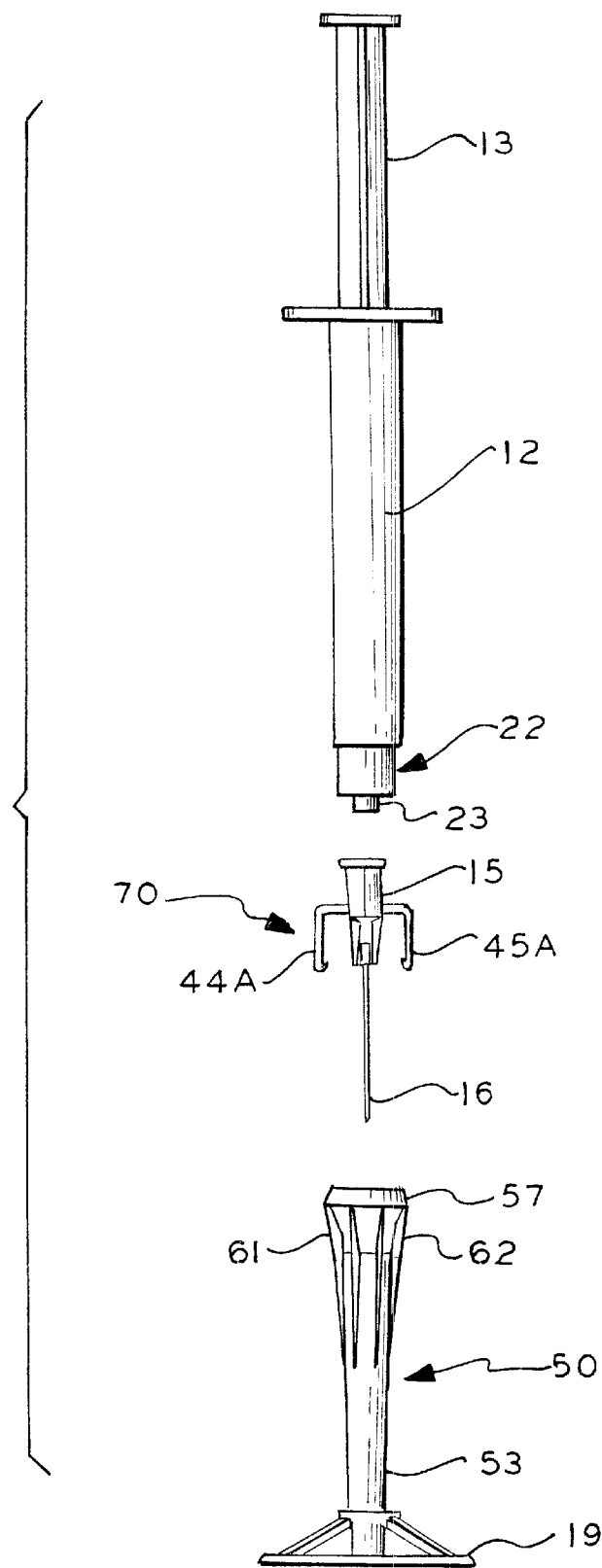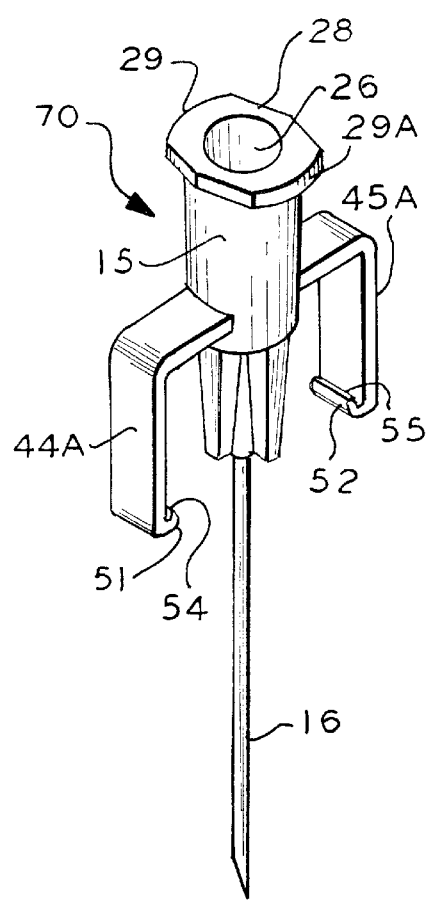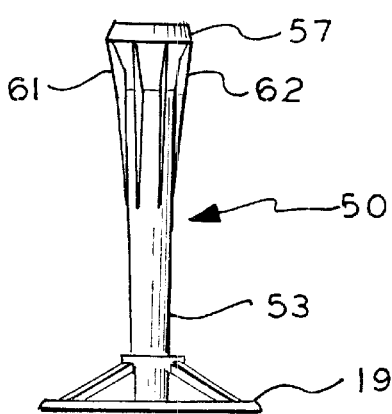

FIG. 21
FIG. 22
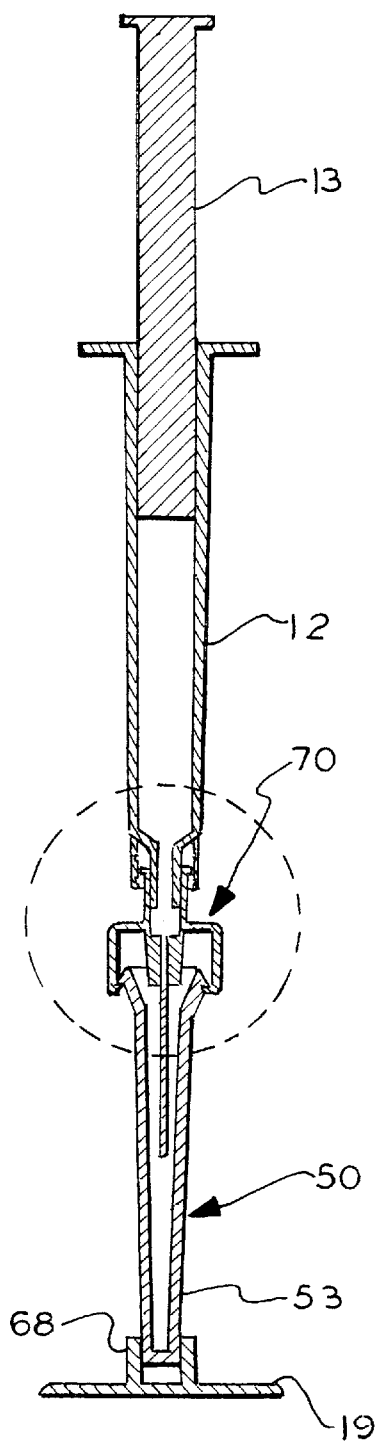
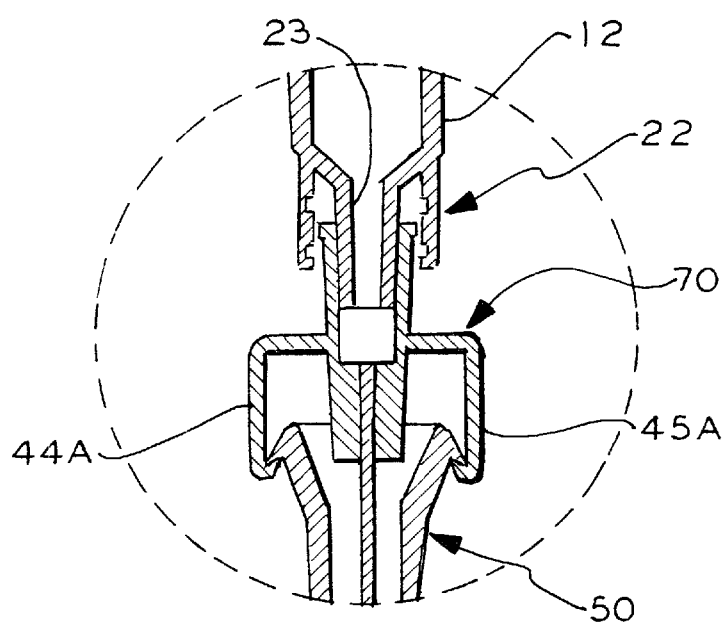

APPARATUS FOR PREVENTING USED HYPODERMIC NEEDLE STICKS

CROSS-REFERENCE TO RELATED APPLICATION

This application is a continuation-in-part application of U.S. patent application Ser. No. 09/577,022 filed May 23, 2000 now abandoned, entitled APPARATUS FOR PREVENTING USED HYPODERMIC NEEDLE STICKS, Leroy D. Geist, inventor, and assigned to the same assignee as the present application.

BACKGROUND OF THE INVENTION

This invention relates generally to apparatus for preventing used hypodermic needle sticks. More particularly, this invention relates to an adapter for being fastened to a needle sheath to lock a used hypodermic needle in the needle sheath; viewed alternatively, this invention relates to an adapter for being fastened to a needle sheath to entrap a used hypodermic needle between the adapter and the needle sheath. Further, this invention relates to a needle sheath for receiving a used hypodermic needle. Still further, this invention relates to the combination of such adapter and such needle sheath. Further, this invention relates to a kit including a syringe barrel, a syringe needle and such adapter and such needle sheath.

Additionally, this invention relates to combination syringe needle and cantilever latching apparatus, such combination in further combination with a needle sheath, and a kit including such combination syringe needle and cantilever latching apparatus, needle sheath and syringe barrel.

After a hypodermic needle has been used to inject a patient, or to draw blood from a patient, and has been withdrawn, the used and exposed hypodermic needle poses a grave risk of infectious disease transmission to the health care provider, doctor, nurse or any other person into whose skin the used hypodermic needle may stick accidentally. This problem is sometimes referred to as needle stick injury or accidental needle stick injury.

Representative prior art apparatus providing a solution to the hypodermic needle stick injury problem is illustrated in FIG. 1 which shows a prior art syringe needle assembly indicated by general numerical designation 10. Assembly 10 includes a syringe barrel 12 in which a plunger 13 is mounted for sliding, reciprocal movement, and a syringe needle indicated by general numerical designation 14 and which syringe needle includes a needle hub 15 and a hypodermic needle or cannula 16 having a pointed or sharp tip 17; the needle hub is provided with external ridges 15A. A protective needle sheath 18 is shown in FIG. 1 for receiving the hypodermic needle 16 after it has been used. The needle sheath 18 is a hollow cylinder closed at the bottom and open at the top. The needle sheath 18 extends upwardly from a pedestal 19 in which the bottom portion of the sheath 18 is typically mounted in a wedged connection. As illustrated in FIG. 1A, the bottom of the needle sheath is typically filled with a suitable gel 20, e.g. silicon, into which the tip 18 of the used hypodermic needle is inserted. Generally it is the gel 20 which retains the used needle 16 in the needle sheath 18. The upper inner portion of the hypodermic needle sheath 18 is provided with a plurality of internal radially disposed ridges 18A for engaging the radially disposed external ridges 15A provided on the lower portion of the needle hub 15.

The syringe barrel 12, FIG. 1, is provided with a male luer lock connector indicated by general numerical designation 22 for leak-proof connection to the needle hub 15. Male luer lock connector 22 is shown in detail and in cross-section in FIG. 2. As shown in FIG. 2, the male luer lock connector 22 includes a central externally tapered male luer 23 surrounded by an annular collar 24 which is spaced radially outwardly from the male luer 23 and provided with an internal thread 25. The needle hub 15, FIG. 2, provides an internally tapered female luer 26 and includes an upper flange 28 provided with diametrically opposed and radially outwardly extending tabs or tab portions 29 and 29A. For leak-proof connection, FIG. 2, the male luer 23 of the syringe barrel connector 22 is inserted into the female luer 26 provided in the needle hub 15 and the needle hub tabs 29 and 30 are threaded into the internal thread 25 provided in the syringe barrel connector 22. Typically this is done by the health care provider who then produces appropriate relative rotational movement between the syringe barrel 12 and the needle hub 15. This rotational movement threads the female luer tabs 29 and 29A upwardly into the internal thread 25 of the male luer lock connector 22 which forces the male luer 23 and the female luer 26 into a wedged or slight interference fit producing a leak-proof connection. This connection is sometimes referred to in the art as a slip fit connection. After such connection, the syringe needle assembly 10, assembled as shown in FIG. 1, is ready for use to inject a patient with a liquid medication or to withdraw blood from the patient.

After use, the health care provider inserts the used needle 16 and the needle hub 15 into the needle sheath 18 (FIG. 1) engaging the external ridges 15A provided on the needle hub 15 with the internal ridges 18A provided in the needle sheath 18 to prevent relative rotation between the needle hub 15 and the needle sheath 18. The heath care provider then provides appropriate relative rotational movement between the syringe barrel 12 and the needle sheath 18, opposite to the relative rotational movement used to connect the male luer lock connector 22 and the needle hub 15, and the needle hub tabs 29 and 29A (FIG. 2) are unthreaded from the internal thread 25 of the male luer lock connector 22 which forces the male luer connector 23 upwardly out of the female luer 26.

As the used hypodermic needle 16 is inserted into the hypodermic needle sheath 18, the used needle tip 17 is inserted into the gel 20 as shown in the needle sheath 18 as the health care provider places the used needle 16 and needle sheath 18 in a medical waste receptacle. If the used needle 16 comes out of the gel 20 and comes out of the needle sheath 18, the health care provider, or other person, must manually replace the used hypodermic needle 16 in the needle sheath 18 or place them separately in the medical waste receptacle. This places the health care provider and housekeeping personnel at risk of needle stick injury.

Numerous other prior art apparatus are known for preventing accidental needle sticks.

SUMMARY OF THE INVENTION

The present invention provides apparatus for locking a used hypodermic needle in a needle sheath; an adapter for locking to a needle sheath to entrap a used hypodermic needle between the adapter and the needle sheath, a needle sheath for receiving a used hypodermic needle, and the combination of such adapter and such needle sheath. A kit including a syringe barrel, a syringe needle and such adapter and such needle sheath. Combination syringe needle and cantilever latching apparatus, such combination in further combination with a needle sheath and a further kit including such combinations and a syringe barrel.

BRIEF DESCRIPTION OF THE DRAWINGS

FIG. 11 is a diagrammatical illustration of a kit embodiment of the present invention;

FIG. 16 is a partial vertical elevational view of the adapter and the needle sheath of the present invention and illustrates the engagement between the adapter cantilever latching members and external ridges provided on the pedestal to prevent rotation between the adapter and the pedestal as the syringe barrel is being removed from the adapter of the present invention;

FIG. 17 is a view taken generally along the line 17—17 in FIG. 16 and in the direction of the arrows, FIG. 17 is not cross-sectioned for clarity of presentation; and FIG. 18 is an exploded, vertical, perspective view of a prior art syringe barrel and combination syringe needle and cantilever latching apparatus embodying the present invention and such combination in further combination with a needle sheath comprising a further combination embodiment of the present invention;

FIG. 19 is an enlarged perspective view of the combination syringe needle and cantilever latching apparatus shown in FIG. 18;

FIG. 21 is a vertical cross-sectional view taken through FIG. 20;

FIG. 22 is an enlarged view of the encircled portion of FIG. 21; and

DESCRIPTION OF THE PREFERRED EMBODIMENTS

Figure 1:
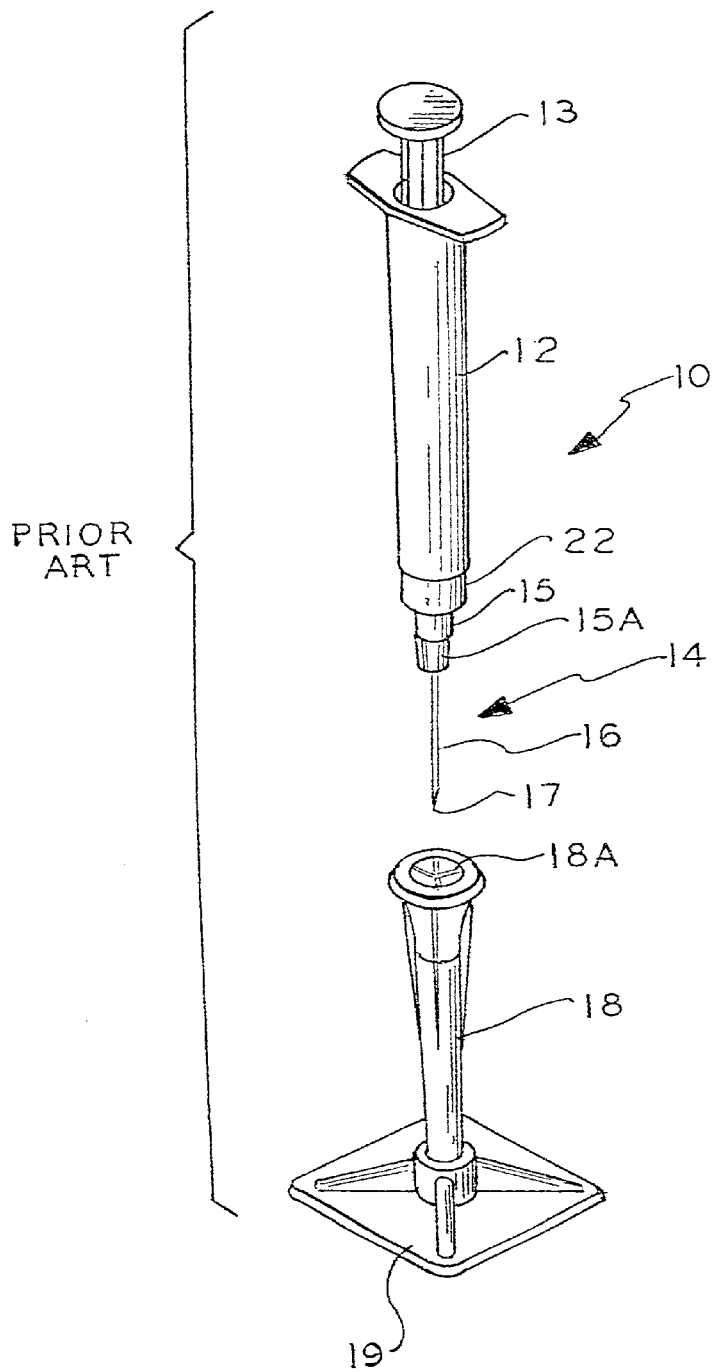
FIG. 1 is a vertical elevational view of prior art apparatus for preventing needle stick injury.
Figure 1A:
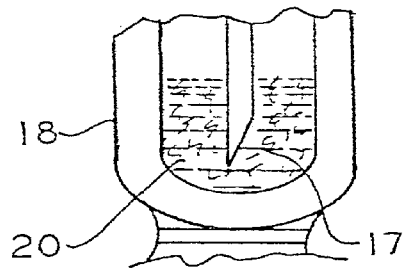
FIG. 1A is an enlarged diagrammatical view of the bottom portion of the needle sheath shown in FIG. 1.
Figure 3:
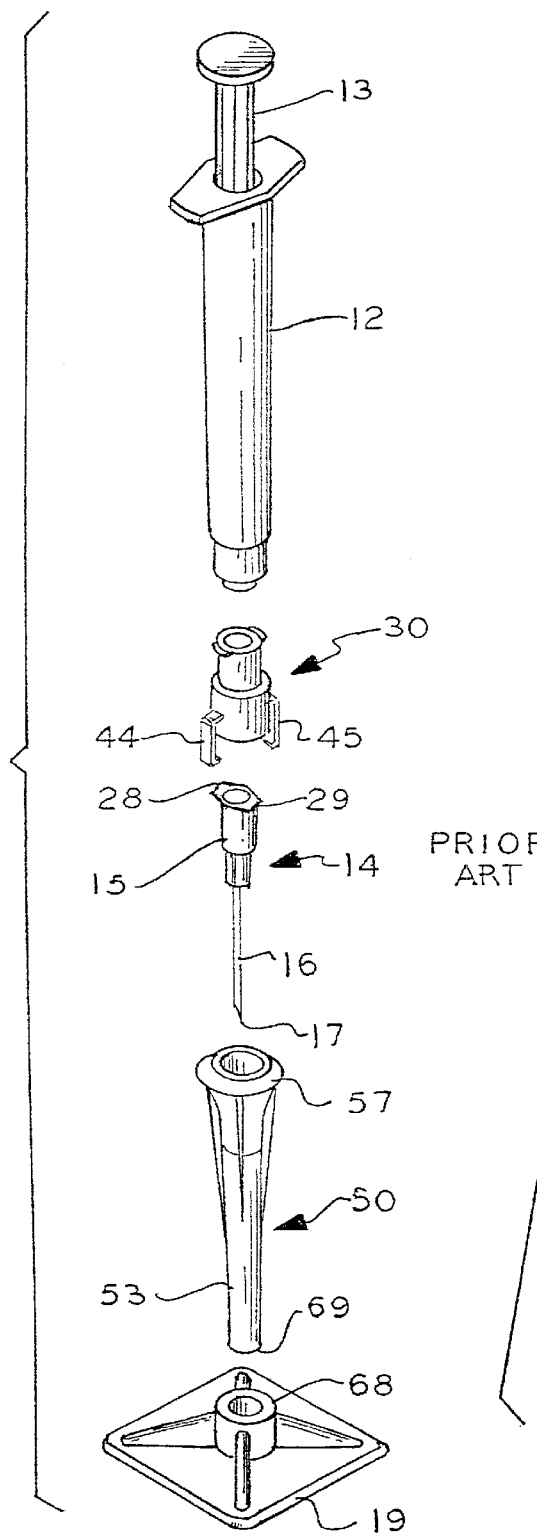
FIG. 3 is an exploded, vertical, perspective view of a prior art syringe barrel, a prior art syringe needle, and an adapter and needle sheath embodying the present invention.

Referring to the exploded view of FIG. 3, there is shown the prior art syringe barrel 12 shown in FIG. 1 and described above, an adapter embodying the present invention and indicated by general numerical designation 30, the prior art syringe needle 14 shown in FIG. 1 and described above, a needle sheath 50 embodying the present invention, and the prior art pedestal 19 shown in FIG. 1 and described above. The adapter 30 comprises an embodiment of the present invention, the needle sheath 50 comprises an embodiment of the present invention, the adapter 30 and needle sheath 50 comprise a combination embodiment of the present invention, and the syringe barrel 12, syringe needle 14, adapter 30 and needle sheath 50 comprise a kit embodiment of the present invention.

Figure 4:
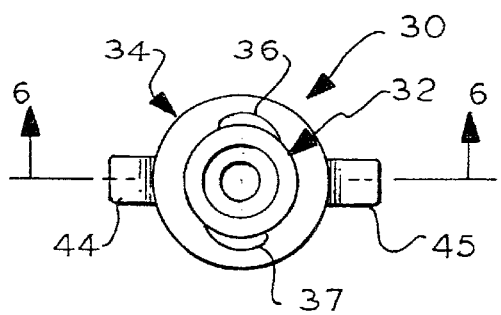
FIG. 4 is a top view of the adapter shown in FIG. 3.
Figure 5:
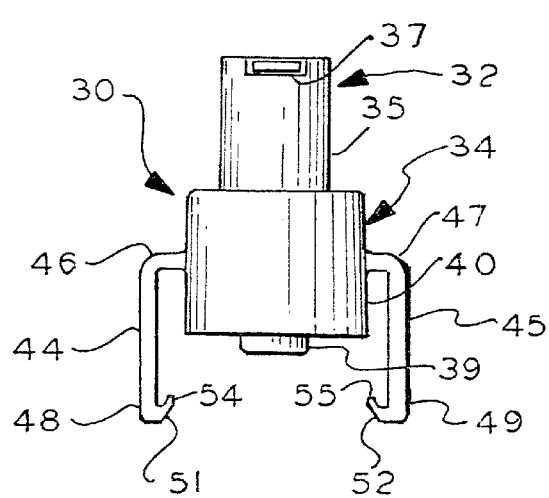
FIG. 5 is a side view of the adapter shown in FIG. 3.
Figure 6:
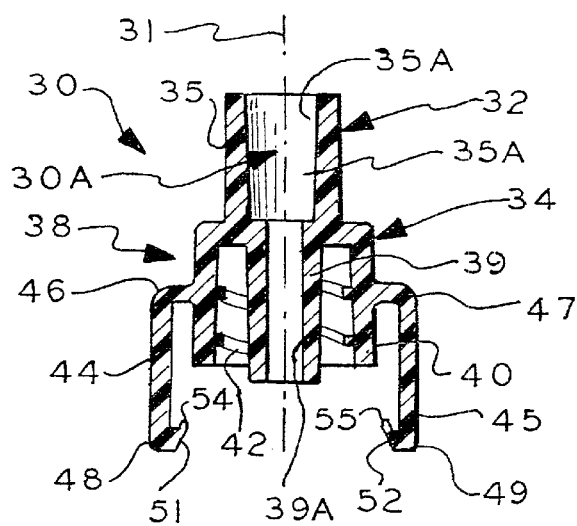
FIG. 6 is a vertical cross-sectional view taken generally along the line 6—6 in FIG. 5 in the direction of the arrows.
Figure 7:
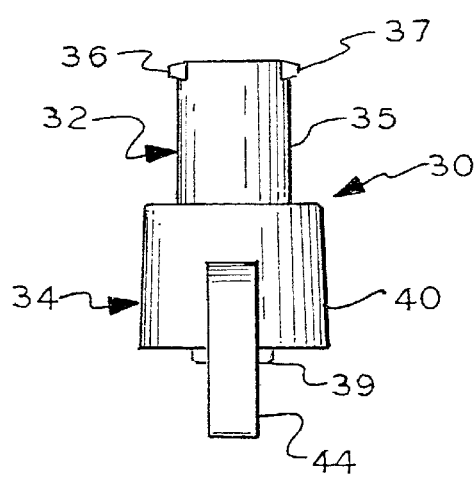
FIG. 7 is a right side or left side view of the adapter shown in FIG. 5.

The structure of the adapter 30 is shown in detail in FIGS. 4–7. As will be understood from these FIGS., the adapter 30 is a generally hollow cylindrical body including opposed top and bottom end portions indicated respectively by general numerical designations 32 and 34 in FIG. 5; the adapter has a central axis 31 shown in FIG. 6. The top end portion 32, FIG. 6, provides an internally tapered female luer connector 35 which may be provided at its outer end portion with a pair of diametrically opposed and radially outwardly extending tabs 36 and 37 as shown in FIG. 7; the female luer connector 35 is provided with a conical inwardly tapered internal surface 35A (FIG. 6) providing a fluid passageway therethrough. The adapter bottom end portion 34, FIG. 6, provides a male luer lock connector indicated by general numerical designation 38 and which includes a central outwardly tapered conical male luer connector 39 surrounded by an annular collar 40 which is spaced radially outwardly from the male luer connector 38 and which is provided with an internal thread 42; the male luer connector 39 is provided with a cylindrical internal surface 39A providing a passageway therethrough. It will be understood that the male luer lock connector 38 generally has the same structure and function as the male luer lock connector 22 shown in FIGS. 1 and 2 and described above.

Referring further to FIGS. 4–7, the bottom end portion 34 of the adapter 30 is provided with a pair of diametrically opposed and radially outwardly extending external resilient cantilever locking or latching members 44 and 45; the latching members 44 and 45 are spaced from each other and are parallel to the adapter axis 31 as shown,in FIG. 6. As will be understood from FIGS. 5, 6 and 7, the resilient cantilever locking or latching members extend generally longitudinally (FIG. 7) and include respective top end portions 46 and 47 extending from the annular collar 40 and respective bottom end portions 48 and 49 which extend axially outwardly beyond the annular collar 40 and the male luer connector 39 as will be understood from FIGS. 4 and 6. The diametrically opposed inner portions of the bottom end portions 48 and 49 of the resilient cantilever locking or latching members 44 and 45 (note FIGS. 5 and 6) are curved outwardly to provide camming surfaces 51 and 52 and are further provided with upwardly extending hook members 54 and 55; the hook members 54 and 55 extend upwardly generally parallel to the intermediate portion of the locking or latching members 44 and 45. As viewed in FIG. 6, in side view the hook member 54 is generally reverse J-shaped and the hook member 55 is generally J-shaped. Referring still further to FIGS. 5, 6 and 7, it will be noted that the top and bottom end portions 32 and 34 of the adapter 30 are generally hollow cylinders and that the outer diameter of the bottom end portion 34 is larger than the outer diameter of the top end portion 32. The adapter 30, in the preferred embodiment, was made by suitable injection molding and made from a suitable thermoplastic material, e.g., polycarbonate. Accordingly, it will be understood that the cantilever locking or latching members 44 and 45 are resilient cantilever locking or latching members permitting them to flex outwardly and return or flex resiliently inwardly to their positions shown in FIGS. 5–7.

Referring again to FIG. 6, it will be understood that the adapter 30 is provided with a generally centrally formed internal liquid passageway for placing the syringe barrel 12 (FIG. 3), needle hub 15 (FIG. 3) and hypodermic needle 16 (FIG. 3) in liquid communication upon being connected to the adapter. More particularly, from FIG. 6 it will be understood that the internal conical surface 35A of the female luer 35 and the internal cylindrical internal surface 39A of the male luer connector 30 cooperatively provide the liquid passageway indicated by general numerical designation 30A in FIG. 6.

Figure 8:
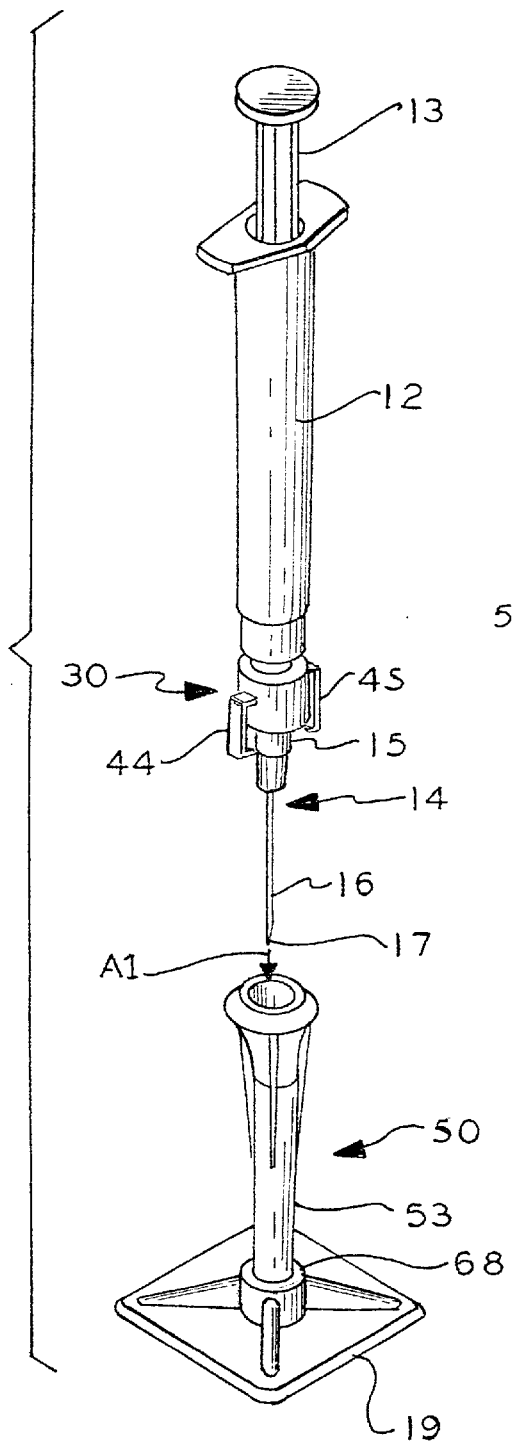
FIG. 8 is an exploded elevational view showing a prior art syringe barrel, the adapter of the present invention connected to the syringe barrel, and illustrating the insertion of a used hypodermic needle in the needle sheath of the present invention.
Figure 9:
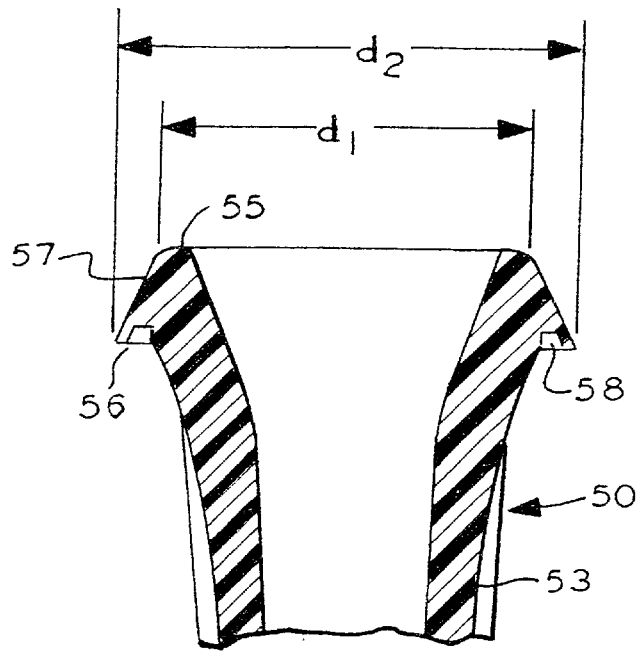
FIG. 9 is a partial vertical cross-sectional view of the upper portion of the needle sheath of the present invention.

The needle sheath 50, FIGS. 3 and 8, comprises a substantially hollow cylinder or tubular member 53 closed at the bottom portion open at the top portion and tapering inwardly from the top portion towards the bottom portion. The needle sheath 50 is for receiving a used hypodermic needle. As will be understood from FIG. 9, the open top portion of the tubular member 53 is an enlarged hollow frusto-conical open top portion including a generally flat annular top surface 55 having a first outer diameter d1, a generally flat annular bottom surface 56 spaced from the top surface 55 and having an outer diameter d2 larger than the diameter d1 and an external inclined surface 57 intermediate and interconnecting said top annular surface 55 and said bottom annular surface 56. The bottom annular surface 56 is provided with an upwardly extending circular groove 58. The inclined surface 57 is a camming surface and also may be understood to be a beveled surface.

As will be understood from FIGS. 3 and 8, the needle sheath 50 may include the pedestal 19 shown in FIG. 1 and described above and which pedestal is provided with an upwardly extending hollow cylinder 68 for receiving the bottom portion 69 (FIG. 3) of the tubular member 53 in a wedged engagement, or interference fit, to support the needle sheath 50 in an upwardly extending vertical position as shown in FIGS. 3 and 8. In the preferred embodiment the needle sheath 50 was formed by suitable injection molding and from a suitable thermoplastic, e.g., acrylic.

Figure 10:
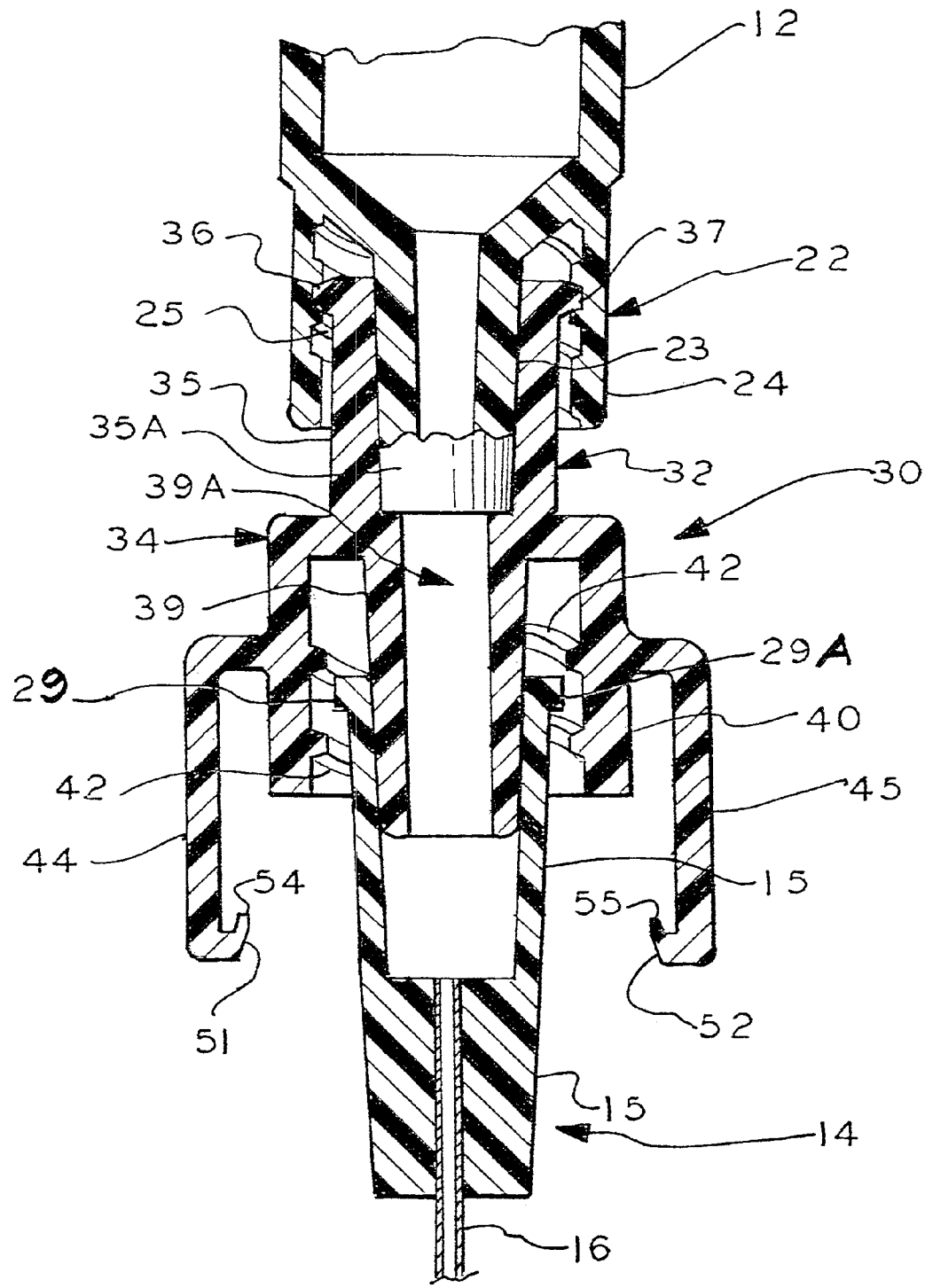
FIG. 10 is a partial vertical, diagrammatic cross-sectional view illustrating the connection of the adapter of the present invention to a prior art syringe barrel and to a prior art syringe needle.

As will be understood primarily from FIG. 10, to threadedly connect the adapter 30 removably to the male luer lock connector 22 of the syringe barrel 12 (FIG. 3), the externally tapered male luer connector 23 provided on the syringe barrel connector 22 is inserted into the internally tapered female luer 35 provided at the top end portion of the adapter 30, by placing the outwardly extending tabs 36 and 37 (FIG. 7) provided at the upper end portion of the adapter female luer 35 into engagement with the internal thread 25 (FIG. 2) provided in the collar 24 of the luer lock connector 22 (FIG. 2), and then by providing relative rotation between the syringe barrel 12 and the adapter 30 to thread the tabs 36 and 37 upwardly into the internal thread 25 to force the externally tapered male luer connector 23 (FIG. 2) into the internally tapered female luer 35 in a leak-proof connection. It will be understood from FIG. 3 that such relative rotation of the syringe barrel 12 and the adapter 30 provides the syringe barrel 12 with relative clockwise rotation as viewed in FIG. 3 and provides the adapter 30 with relative counter clockwise rotation as viewed in FIG. 3.

Referring further primarily to FIG. 10, to connect the adapter 30 to the syringe needle 14, the adapter male luer 39 (FIG. 6) is inserted into the needle hub female luer 26 (FIG. 2) and the needle hub tabs 29 and 29A are placed in engagement with the adapter internal thread 42 and relative rotation is provided between the adapter 30 and the syringe needle 14 to thread the hub tabs 29 and 29A upwardly into the adapter internal thread 42 to force the externally tapered adapter male luer 39 into the hub interiorly tapered female luer 26 in a leak-proof connection.

Upon the adapter 30 being connected removably to the syringe barrel connector 22, and thereby to the syringe barrel; 12, the syringe barrel 12, adapter 30, and syringe needle 14, including the needle hub 15 and hypodermic needle 16, occupy the positions shown in the upper portion of FIG. 8. The kit embodiment of the present invention, referring again to FIG. 8, may include the syringe barrel 12 with the plunger 13, the adapter 30, the syringe needle 14 and the needle sheath 50; such kit may include the syringe barrel 12, adapter 30 and syringe needle 14 disconnected from each other or such elements may be interconnected as shown in FIG. 8 and described above and comprising the kit. As shown in FIG. 11, the kit embodiment of the present invention may further include a tray or receptacle T for receiving and containing the syringe barrel 12, adapter 30 and syringe needle 14, either disconnected or connected, the needle sheath tubular member 53 and the pedestal 19. The kit may further include a suitable package, indicated diagrammatically in FIG. 11 by the irregular line and identified by the letter P. Such packaging may be any suitable.packaging known to the art and may be, for example, a suitable relatively flexible metal or metallized material for preventing contaminants such as a bacteria and virus from passing therethrough Typically, the syringe barrel 12, adapter 30 and syringe needle 14 are provided from the supplier and to the user, or health care provider, with the syringe barrel 12, adapter 30 and syringe needle 14 interconnected as shown in FIG. 8 and as described above. Ready to draw a blood sample from a patient, or to be filled with a liquid medication which is injected into the patient; the hypodermic needle 14 is as supplied may be covered with a tubular protective cap as known to the art.

Figure 12:
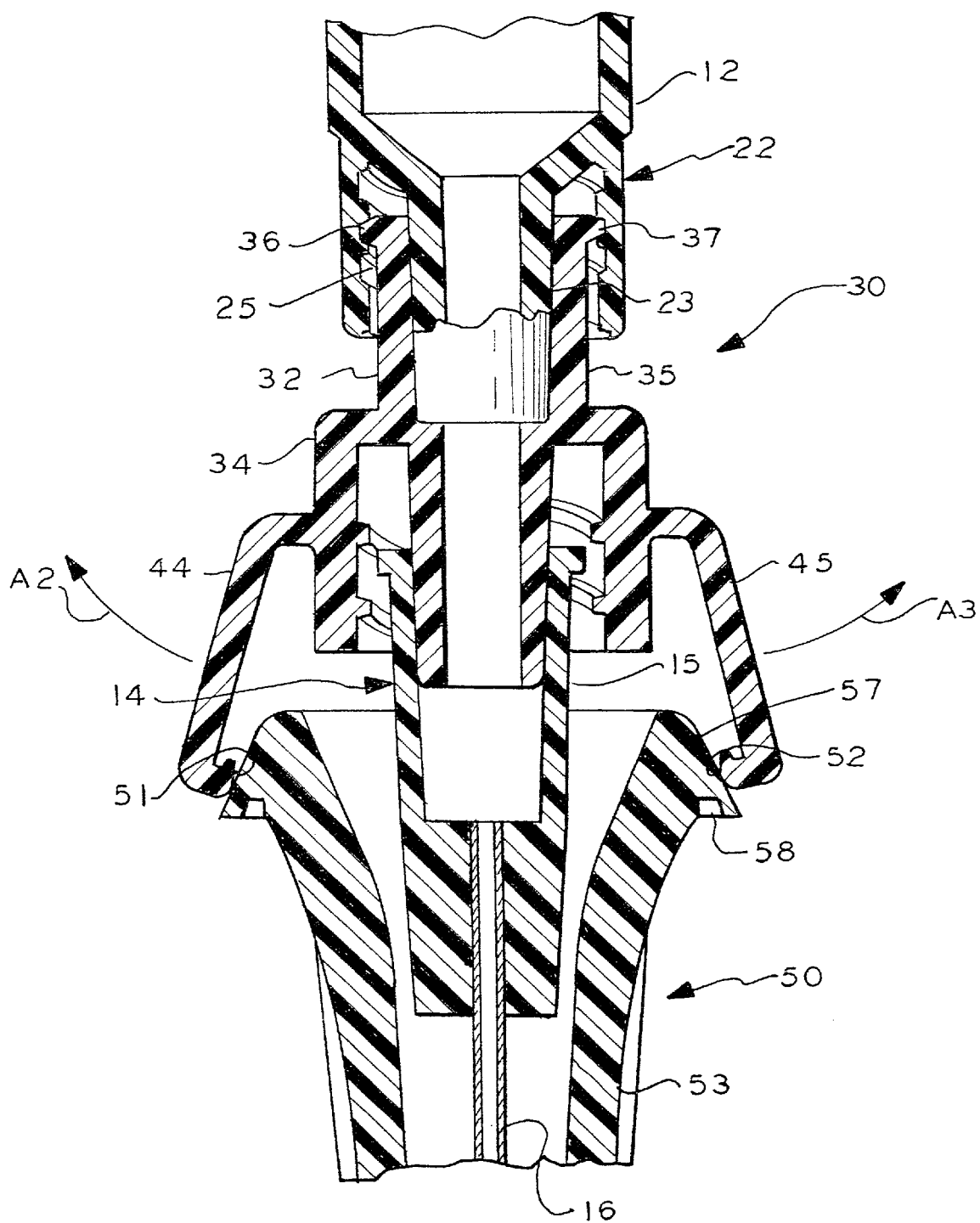
FIGS. 12 and 13 are partial vertical diagrammatical cross-sectional views illustrating the locking of the adapter of the present invention to the needle sheath of the present invention.
Figure 13:
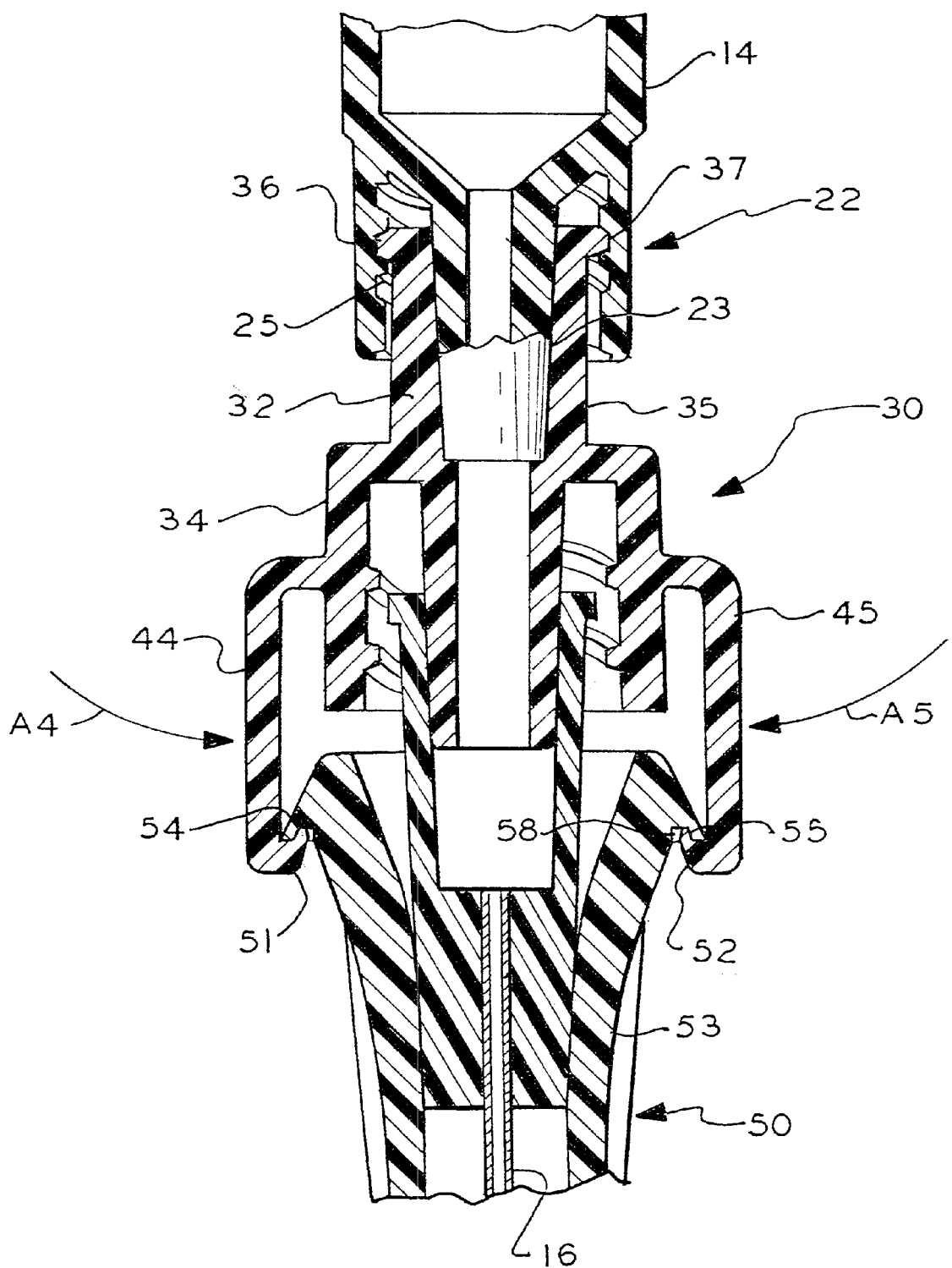

After use in either drawing a blood sample from a patient or injecting a patient with a liquid medication, as illustrated generally in FIG. 8, the syringe barrel 12, adapter 30, needle hub 15 and the now used hypodermic needle 16 are placed vertically over the needle sheath 50. The used hypodermic needle 16 and the needle hub 15 are inserted downwardly, as indicated by the arrow A1 in FIG. 8 into the tubular member 53 of the needle sheath 50 causing, as shown in FIG. 12, the camming surfaces 51 and 52 provided at the bottom portions of the resilient locking or latching members 44 and 45 to engage the camming surface provided by the inclined or beveled surface 57 of the upper enlarged frusto-conical top portion of the needle sheath 50 which causes the lower portions of the flexible cantilever locking or latching members, as indicated by the arrows A2 and A3 in FIG. 12 to flex outwardly which permits, or facilitates, the lower portions of the resilient cantilever locking or latching members 44 and 45 to pass downwardly over the enlarged upper frusto-conical portion of the needle sheath 50 and pass thereunder, as shown in FIG. 13, which permits the lower portions of the locking or latching members 44 and 45 to flex inwardly, as illustrated by the arrows A4 and A5 in FIG. 13, causing the hook members 54 and 55 of the lower portions of the cantilever locking or latching members 44 and 45 to be inserted into the circular groove 58 as shown in FIG. 13. Upon the hook members 54 and 55 being inserted into the circular groove 58, the adapter 30 is locked to the needle sheath 50 and the used hypodermic needle 16 is entrapped between the adapter 30 and the needle sheath 50 preventing accidental needle sticks from the used hypodermic needle.

Figure 14:
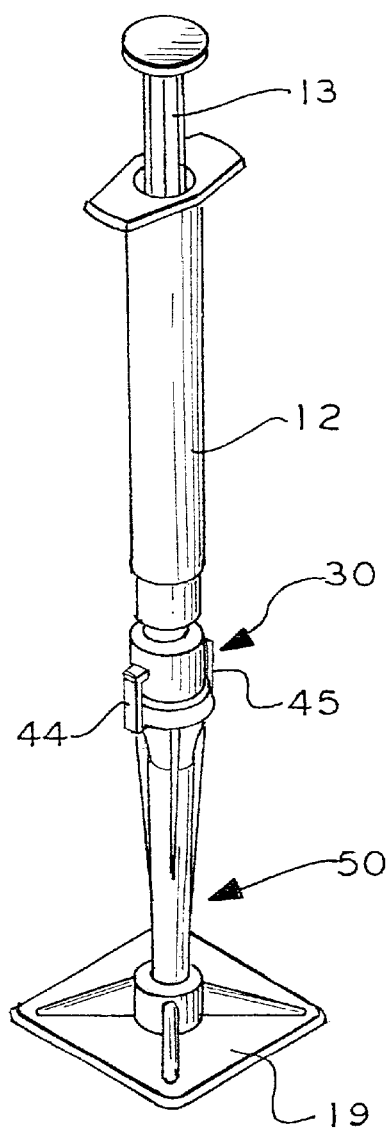
FIG. 14 is a vertical elevational view, in perspective, showing a prior art syringe barrel connected to the adapter of the present invention which is locked to the needle sheath of the present invention.

The syringe barrel 12 is unthreaded and removed from the adapter 30, as shown in FIG. 15, by, and referring again to FIGS. 13 and 14, rotating the syringe barrel 12 with respect to the adapter 30 and in the counter clockwise direction as viewed in these FIGS. to unthread the adapter female luer tabs 36 and 37, FIGS. 4 and 6, from the internal thread 25 (FIG. 2) provided in the luer lock connector 22 which pulls the male luer connector 23, provided on the luer lock connector 22, upwardly out of the female luer 35 provided at the top end of the adapter 30. To prevent rotation of the adapter 30 with respect to the needle sheath 50 as the syringe barrel is rotated with respect to and rotated and removed from the adapter 30, as described above, the cantilever locking or latching members 44 and 45 engage a pair of diametrically opposed and outwardly extending ridges 61 and 62, note FIGS. 16 and 17, provided on the needle sheath tubular member 53, and which engagement prevents the adapter 30 from rotating with respect to the needle sheath 50. As the syringe barrel 12 is being rotated with respect to, and removed from, the adapter 30, it may be necessary for the health care provider to hold the needle sheath 50 and pedestal 19 stationary.

Figure 15:
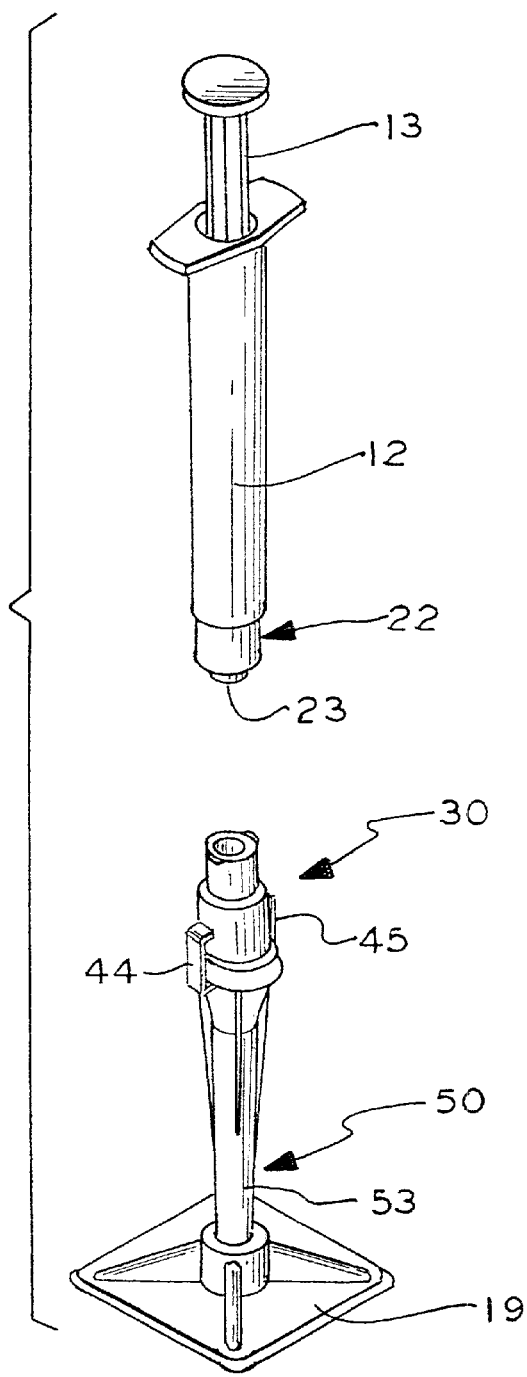
FIG. 15 is a vertical perspective view showing the prior art syringe barrel removed from the adapter of the present invention.

As will be understood generally from FIG. 15, the used hypodermic needle 16 (FIG. 13) is now firmly entrapped in the needle sheath 50 between the adapter 30 and the needle sheath 50 thereby preventing the used hypodermic needle 16 from accidentally sticking the health care provider, or any other person, and thereby preventing the above-noted accidental needle stick injury. The adapter 30 and the needle sheath 50 with the used hypodermic needle 16 firmly trapped inside may be placed in a suitable medical waste receptacle; the pedestal 19 may also be so disposed or the pedestal 19 may be removed from the needle sheath 50 for subsequent re-use.

Figure 20:
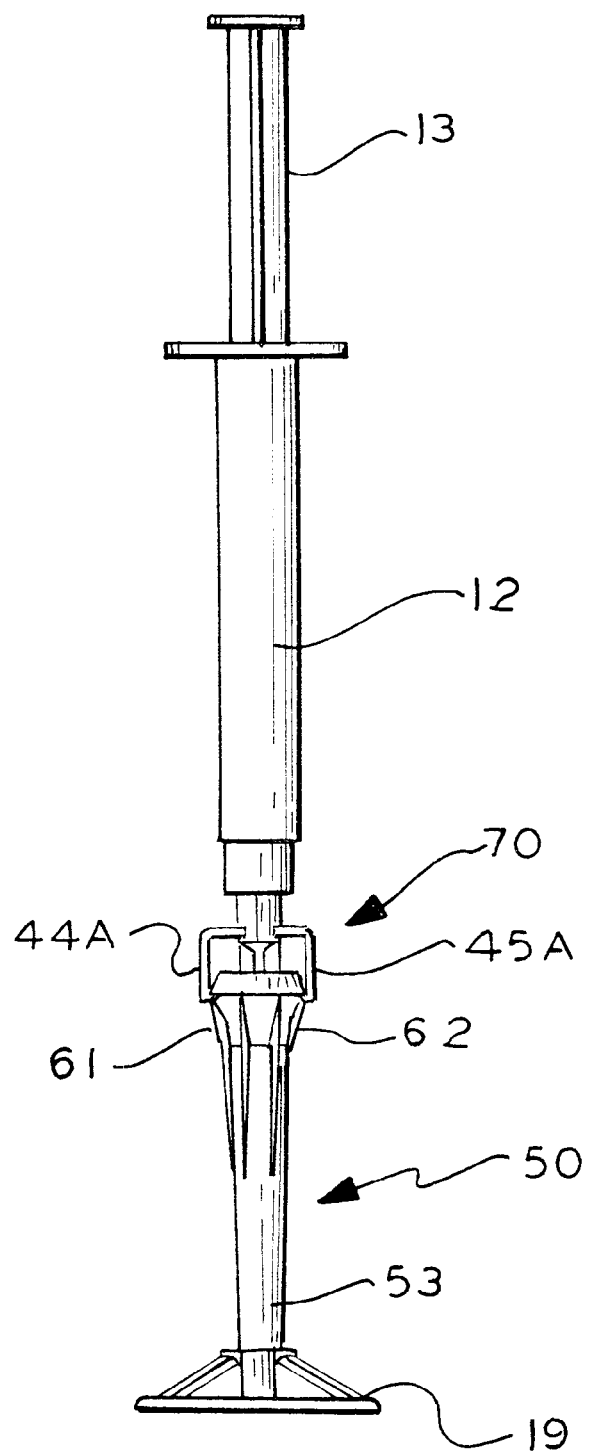
FIG. 20 is a vertical elevational view showing a prior art syringe barrel connected to the combination syringe needle and cantilever apparatus of the present invention which is shown latched to the needle sheath of the present invention.

Referring again to FIGS. 3–7, and in particular to FIG. 3, it will be understood that the syringe needle 14 and adapter 30 comprise a first embodiment of combination syringe needle and cantilever latching apparatus of the present invention and that a second embodiment of combination syringe needle and cantilever latching apparatus of the present invention is shown in FIGS. 18–21, in particular FIG. 19, and is indicated by general numerical designation 70. Also shown in FIGS. 18, 19 and 21 is the prior art syringe barrel 12 including the plunger 13, male luer lock connector 22 and tapered male luer 23 and which is described above and shown particularly in FIGS. 1 and 15, particularly FIG. 15. Also shown in FIGS. 18, 20 and 21 is the needle sheath 50 of the present invention described above and shown in FIGS. 3 and 8, particularly FIG. 8. It will be understood that the needle sheath 50 shown in FIGS. 18, 20 and 21 is the same as needle sheath 50 shown in FIGS. 8 and 15 and includes the same component elements and performs the same function as the needle sheath 50 as described above with regard to the adapter 30.

Referring to the detailed structure of the combination syringe needle and cantilever apparatus 70, and to FIGS. 18 and 19 and in particular to FIG. 19, the combination syringe needle and cantilever apparatus 70 includes a needle hub 15, a hypodermic needle 16 and a pair of diametrically opposed and radially outwardly extending resilient cantilever locking or latching members 44A and 45A. It will be understood that the cantilever latching members 44A and 45A include the same elements, namely, the camming surfaces 51 and 52 and the upwardly extending hook members 54 and 55 as do the cantilever latching members 44 and 45 shown in FIGS. 4–7 and as described above. As will be understood particularly from FIG. 19, the resilient cantilever latching members 44A and 45A include upper portions formed integrally with the upper portion of the needle hub 15 and lower portions extending along and spaced from the lower portion of the needle hub and providing the above-noted upwardly extending hook members 54 and 55. From FIG. 19 it will be further understood that the cantilever latching members 44A and 45A extend along and are spaced from the lower portion of the needle hub 15.

Figure 2:
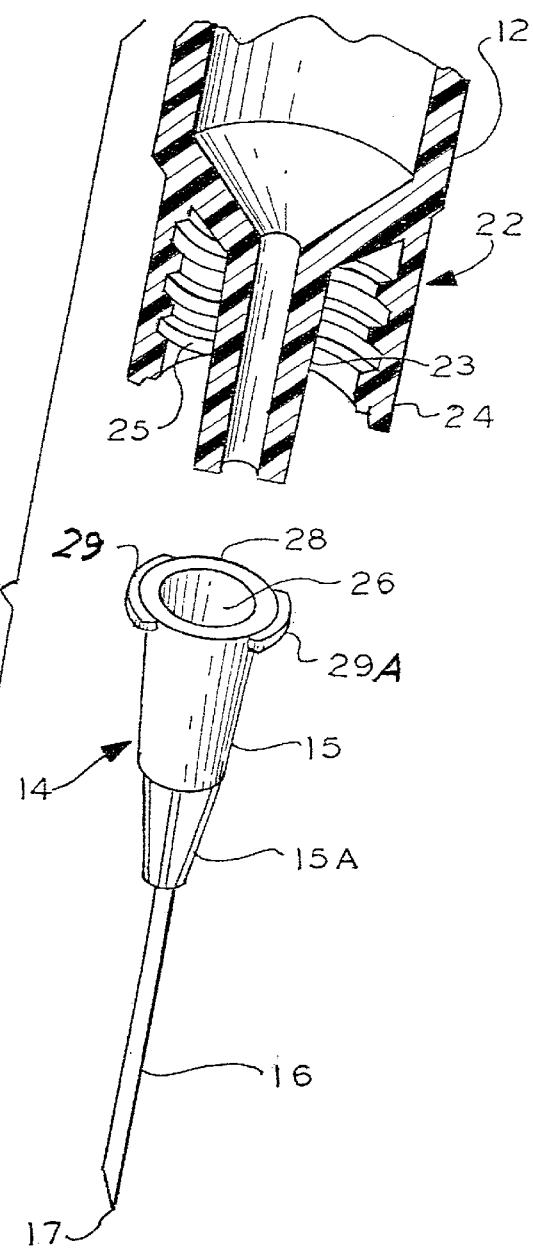
FIG. 2 is an enlarged, exploded, partial perspective view of a prior art syringe needle including a hub and a hypodermic needle, and a male luer lock connector provided at the end of a syringe barrel.

Needle hub 15, FIG. 19, provides an inwardly tapered female luer connector 26 and includes a pair of diametrically opposed and radially outwardly extending tabs or tab portions 29 and 29A. The female luer connector 26 and the luer tabs 29 and 29A are for connecting the needle hub 15 to the male luer lock connector 23, FIG. 18, provided on the syringe barrel 12 in the same manner that the female luer 35 and tabs 36 and 37 of the adapter 30 (FIGS. 5–7) are connected to the male luer lock connector 23 provided on the syringe barrel 12 as shown in FIGS. 2 and 10 and as described above, namely, by producing relative rotational movement between the combination syringe needle and cantilever latching apparatus 70 and the syringe barrel 12.

After the hypodermic needle 16 has been used to draw blood or inject a patient with a liquid medication, the used hypodermic needle 16 is placed vertically over the needle sheath 50 as shown in FIG. 18, and the used hypodermic needle 16 is inserted into the needle sheath 50 as shown in FIGS. 20 and 21. It will be understood that the resilient cantilever latching members 44A and 45A function in the same manner as the cantilever latching members 44 and 45 described above and shown particularly in FIGS. 12 and 13, to lock or latch the combination syringe needle and cantilever latching apparatus 70 sufficiently tightly to the needle sheath 50, and non-rotatably due to the engagement of the cantilever latching members 44A and 45A with the outwardly extending external ridges 61 and 62 provided on the needle sheath 50, to entrap the used hypodermic needle 16 within the needle sheath 50, particularly as shown in FIG. 21, and to permit the syringe barrel 12 to be rotated with respect to the combination syringe needle and cantilever apparatus 50 to disconnect luer lock connection between the syringe barrel 12 and the combination syringe needle and cantilever latching apparatus 70 to permit the syringe barrel to be removed from the combination syringe needle and cantilever latching apparatus 70 without unlocking or unlatching the combination syringe needle and cantilever latching apparatus 70 from the needle sheath 50. Accordingly, as shown particularly in FIG. 21, the used needle 16 is entrapped in the needle sheath 50 preventing accidental used needle sticks and the needle sheath and the combination syringe needle and cantilever latching apparatus 50 may be placed in a suitable medical waste receptacle; the pedestal 19 also may be so disposed of or the pedestal 19 may be removed from the needle sheath 50 for subsequent reuse.

It will be further understood, FIGS. 18 and 19, that the needle hub 15 may not include the ,opposed hub tabs 29 and 29A and may only provide an inwardly tapered female slip luer connector for a leak-proof slip fit engagement with an outwardly tapered male luer provided on a syringe barrel.

Figure 23:
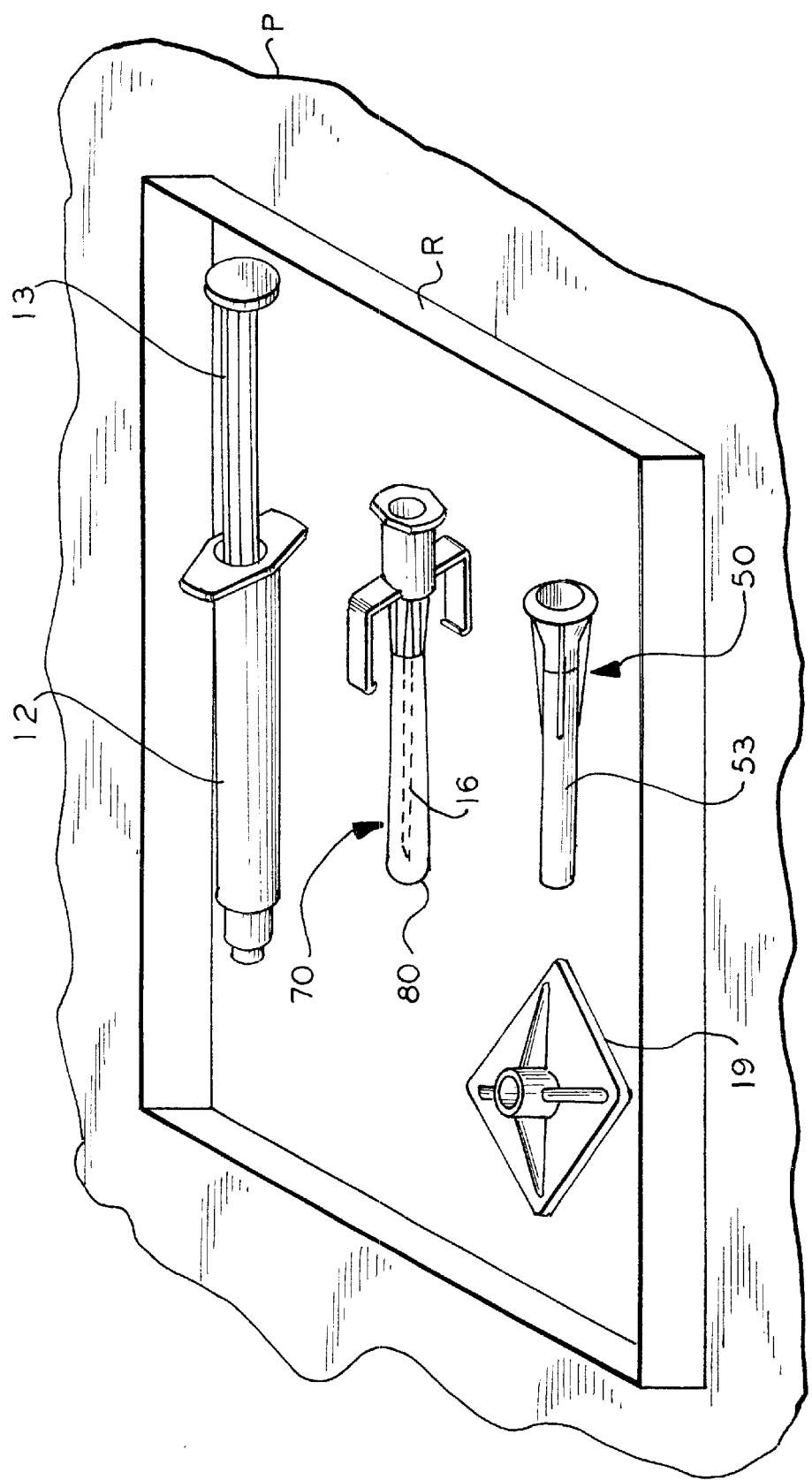
FIG. 23 is a diagrammatical illustration of an alternate kit embodiment of the present invention.

Referring to FIG. 23, a further and alternate kit embodiment of the present invention is shown in FIG. 23 and may include a tray or receptacle R for receiving and containing the syringe barrel 12, combination syringe needle and cantilever latching apparatus 70, tubular member 53 comprising the needle sheath 50 and the needle sheath pedestal 19. The hypodermic needle 16 of the combination syringe needle and cantilever latching apparatus 70 may come covered with a prior art sheath 80, typically made of plastic, for initially covering the hypodermic needle 16 during shipment and prior to use and for preventing needle sticks during such period. This kit may further include a suitable package, indicated diagrammatically by the irregular line and identified by the letter P. Such packaging may be any suitable packaging known to the art and may be, for example, a suitable relatively flexible metal or metallized material for preventing contaminants such as bacteria and virus from passing therethrough.

It will be understood, by those skilled in the art that many variations and modifications may be made in the present invention without departing from the spirit and scope thereof.

What is claimed is:

1. Apparatus for use with a syringe barrel and with a syringe needle including a needle hub and a hypodermic needle, said apparatus for locking the hypodermic needle in a needle sheath after use, comprising:
    locking means for being connected to the syringe barrel and for being connected to the needle hub, said locking means for providing fluid flow communication between the syringe barrel and the syringe needle, and said locking means including resilient cantilever latching members for locking the locking means to the needle sheath as the hypodermic needle is being inserted therein after use to entrap the hypodermic needle between the locking means and the needle sheath.

2. Apparatus for locking a used hypodermic needle within a needle sheath, comprising:
    a generally hollow cylindrical body having opposed end portions, one end portion providing a first luer connector and the other end portion providing a second luer connector;
    said other end portion provided with a pair of external and diametrically opposed resilient cantilever latching members for locking the body to the needle sheath; and
    said luer connectors cooperatively providing a fluid flow passageway through said body.

3. The apparatus according to claim 2 wherein said first luer connector comprises an inwardly tapered female luer connector for being connected to the syringe barrel in a luer slip connection.

4. The apparatus according to claim 2 wherein said first luer connector comprises an inwardly tapered female luer connector including a pair of outwardly extending and diametrically opposed lugs and is for being connected to the syringe barrel in a luer lock connection.

5. The apparatus according to claim 2 wherein said second luer connector comprises a male luer lock connector for being connected to the needle hub in a luer lock connection.

6. The apparatus according to claim 2 wherein said second luer connector comprises an outwardly tapered male luer connector being connected to the needle hub in a luer slip connection.

7. The apparatus according to claim 2 wherein said cantilever latching members in side view are shaped substantially in the form of a pair of square brackets.

8. Apparatus for use with a syringe barrel, a syringe needle including a needle hub and a hypodermic needle and a needle sheath, said apparatus for locking the hypodermic needle within the needle sheath upon being inserted therein after use, comprising:
    a generally cylindrical body having a generally centrally formed fluid passageway extending therethrough, said body including a first end portion and a second end portion, said end portions being opposed, said first end portion providing a first luer connector for being connected threadedly to the syringe barrel and said second end portion providing a second luer connector for being connected to the needle hub, said second end portion provided with a pair of external and generally diametrically opposed resilient cantilever latching members, said fluid passageway for providing fluid communication between the syringe barrel and the needle hub and the hypodermic needle upon being connected to said body, said cantilever latching members for the needle sheath to lock the hypodermic needle within the sheath upon the hypodermic needle being inserted therein after use, and said cantilever latching members for engaging the needle sheath to prevent rotation between said body and the needle sheath to permit the syringe barrel to be unthreaded from said body without unlocking said body from the needle sheath.

9. The apparatus according to claim 8 wherein said first end portion generally comprises a first hollow cylinder having a first diameter and wherein said second end portion generally comprises a second hollow cylinder having a second diameter larger than said first diameter.

10. The apparatus according to claim 8 wherein said cantilever latching members comprise a pair of generally opposed longitudinally extending cantilever latching members including opposed end portions, one end portion of each cantilever latching member mounted to said second end portion of said body and the other end portion of each cantilever latching member extending outwardly beyond said second end portion of said body and including a hook portion for locking to the needle sheath.

11. The apparatus according to claim 8 wherein said first luer connector comprises an inwardly tapered hollow generally cylindrical female luer slip connector.

12. The apparatus according to claim 8 wherein said first luer connector comprises an inwardly tapered generally hollow cylindrical female luer connector having an outer end portion provided with a pair of diametrically opposed and radially outwardly extending tabs.

13. The apparatus according to claim 8 wherein said second luer connector comprises a male luer lock connector.

14. The apparatus according to claim 8 wherein said first luer connector comprises an outwardly tapered generally hollow cylindrical male luer slip connector.

15. The apparatus according to claim 12 wherein said male luer lock connector includes an externally tapered hollow generally cylindrical male luer connector and a collar surrounding and spaced radially outward from said male luer connector and provided with an internal thread.

16. The apparatus according to claim 8 wherein said body and said resilient cantilever latching members are formed integrally.

17. The apparatus according to claim 16 wherein said body and said resilient cantilever latching members are made of a thermoplastic material.

18. Apparatus for locking a used hypodermic needle in a needle sheath, comprising:

a body having a central axis and provided with a centrally formed axial passageway extending therethrough, said body including a first cylindrical end portion having a first outer diameter and an opposed second cylindrical end portion having a second outer diameter larger than said first outer diameter, said cylindrical end portions providing luer connectors, said body including a pair of external diametrically opposed longitudinally extending resilient cantilever latching members spaced from each other and extending parallel to said central axis, said latching members including inner end portions and outer end portions, said inner end portions of said latching members extending from said second cylindrical end portion and the outer end portion of one of said latching members being J-shaped in side view and the outer portion of the other of said latching members being reversed J-shaped in side view.

19. Combination apparatus for use with a syringe barrel and with a hypodermic needle extending from a needle hub, and for preventing accidental needle sticks from the hypodermic needle after use comprising:

a needle sheath including an outwardly extending enlarged upper portion providing a first camming surface and including an under surface into which a groove extends upwardly, said needle sheath provided with a pair of opposed and outwardly extending ridges;

an adapter for being threaded into engagement with the syringe barrel, for being connected to said needle hub and for providing liquid communication between the syringe barrel and the needle hub and the hypodermic needle, said adapter means provided with a pair of opposed resilient cantilever latching members including lower portions providing a pair of inwardly extending hook members and a pair of second camming surfaces for engaging said first camming surface as said hypodermic needle is being inserted into said needle sheath and as said lower portions of said cantilever latching members pass over said enlarged upper portion of said needle sheath and said lower portions of said cantilever latching members flexing inwardly after said lower portions of said cantilever latching members pass over said enlarged upper portion of said needle sheath to cause said hook members to be inserted into said groove to entrap the hypodermic needle between said adapter and said needle sheath and to fasten said adapter to said needle sheath, said lower portions of said latching members for engaging said ridges to prevent rotation between said adapter and said needle sheath to permit the syringe barrel to be unthreaded from said adapter without unfastening said adapter means from said needle sheath.

20. Combination apparatus for use with a syringe barrel and for use with a syringe needle including a needle hub and a hypodermic needle, said apparatus for preventing accidental needle sticks from the hypodermic needle after use, comprising:

a needle sheath;

an adapter for being threadedly connected to the syringe barrel and for being connected to the needle hub, said adapter for providing liquid communication between the syringe barrel and the syringe needle, said needle sheath and said adapter provided with cooperative means for fastening said adapter to said needle sheath to entrap the hypodermic needle in said needle sheath between said adapter and said needle sheath, and said cooperative means for preventing rotation between said adapter and said needle sheath to permit said syringe barrel to be unthreaded from said adapter without unfastening said adapter from said needle sheath.

21. The apparatus according to claim 20 wherein said needle sheath comprises a tubular member including an open top portion and a closed bottom portion, said open top portion being flared outwardly and including an enlarged hollow, generally frusto-conical portion having an underside provided with an upwardly extending circular groove.

22. The apparatus according to claim 21 wherein adapter comprises:

a generally cylindrical body having a generally centrally formed fluid passageway extending therethrough for providing said fluid communication between the syringe barrel and the needle hub and the hypodermic needle, said body including a first cylindrical end portion and a second cylindrical end portion, said end portions being opposed, said first end portion providing a first luer connector for being threadedly connected to the syringe barrel upon relative rotation therebetween and said second cylindrical end portion providing a second luer connector for being connected to the needle hub upon relative rotation therebetween, said second cylindrical end portion provided with a pair of external and generally diametrically opposed resilient cantilever latching members including outer end portions provided with upwardly extending hook members, said outer end portions of said latching members for engaging said frusto-conical portion of said needle sheath means to cause said outer end portions of said latching members to flex outwardly as said hypodermic needle is being inserted into said needle sheath means after use to permit said hook members to pass over said frusto-conical portion of said sheath means and said outer end portions of said latching members for flexing inwardly after said hook members pass over said frusto-conical portion to cause said hook members to be inserted into said circular groove to fasten said body to said frusto-conical portion to entrap the hypodermic needle within the tubular member upon the hypodermic needle being inserted therein after use, said hook members and said circular groove comprising said cooperative means, said tubular member provided with a plurality of outwardly extending ridges for engaging said outer end portions of said cantilever latching members to prevent rotation of said body with respect to and the unfastening of said body from said tubular member while said syringe barrel is being rotated with respect to said body to unthread said syringe barrel from said first luer connector, said lower portion of said latching member and said ridges further comprising said cooperative means.

23. The apparatus according to claim 22 wherein said first cylindrical end portion generally comprises a first hollow cylinder having a first outer diameter and wherein said second cylindrical end portion generally comprises a second hollow cylinder having a second outer diameter larger than said first outer diameter.

24. The apparatus according to claim 22 wherein said cantilever latching members comprise a pair of generally opposed longitudinally extending cantilever latching members having opposed end portions, one end portion of each cantilever latching member mounted to said second cylindrical end portion of said body and the other end portion of each cantilever latching member extending outwardly beyond said second cylindrical end portion of said body and including a hook member for being received within said circular groove.

25. The apparatus according to claim 22 wherein said first luer connector comprises an inwardly tapered generally hollow cylindrical female luer connector.

26. The apparatus according to claim 22 wherein said first luer connector comprises an inwardly tapered generally hollow cylindrical female luer connector having an outer end portion provided with a pair of diametrically opposed and radially outwardly extending tabs.

27. The apparatus according to claim 22 wherein said second luer connector comprises a male luer lock connector.

28. The apparatus according to claim 27 wherein said male luer lock connector includes an externally tapered male luer connector and a collar surrounding and spaced radially outward from said male luer connector and provided with an internal thread.

29. The apparatus according to claim 22 wherein said second luer connector comprises an outwardly tapered male luer slip connector.

30. The apparatus according to claim 22 wherein said body and said resilient cantilever latching members are formed integrally.

31. The apparatus according to claim 30 wherein said body and said cantilever latching members are formed from a thermoplastic material.

32. The apparatus according to claim 20 wherein said apparatus further comprises support means for engaging said closed bottom portion of said tubular member and for supporting said tubular member in an upwardly extending vertical position.

33. The apparatus according to claim 32 wherein said support means comprise a pedestal provided with an upwardly extending, centrally located hollow cylinder for receiving said bottom portion of said tubular member in an interference fit.

34. An adapter, comprising:
  a body including a first body portion and a second body portion opposed to said first body portion, said first body portion providing a first luer connector and said second body portion providing a second luer connector;
  a pair of external and opposed cantilever latching members including first portions mounted to said second body portion and second portions extending beyond said second body portion and including upwardly extending hook portions; and
  said first body portion and said second body portion cooperatively providing an internal fluid passageway extending through said body.

35. The adapter according to claim 34 wherein said first luer connector comprises an inwardly tapered female luer connector and wherein said second luer connector comprises a male luer lock connector.

36. The apparatus according to claim 34 wherein said pair of cantilever latching members are a pair of longitudinally extending cantilever latching members including intermediate portions intermediate said first end portions and said second end portions of said cantilever latching members, wherein said hook portions extend upwardly substantially parallel to said intermediate portions.

37. The apparatus according to claim 34 wherein said first body portion is a hollow cylindrical first body portion having a first outer diameter and wherein said second body portion is a hollow cylindrical second body portion having a second outer diameter larger than said first outer diameter.

38. A kit comprising:
  a syringe barrel;
  a syringe needle including a needle hub and a hypodermic needle;
  a needle sheath;
  an adapter including a first end portion and a second end portion opposite said first end portion, said first end portion providing a first luer connector for being connected removably to said syringe barrel and said second end portion providing a second luer connector for being connected to said needle hub, said second end portion provided with a pair of external and generally diametrically opposed resilient cantilever latching members, said adapter having a generally centrally centrally formed fluid passageway extending therethrough for providing fluid communication between said syringe barrel and said syringe needle upon being connected to said body, said cantilever latching members for locking said adapter to said needle sheath to entrap said hypodermic needle within said needle sheath upon said hypodermic needle being inserted therein after use; and
  said needle sheath provided with a pair of diametrically opposed and outwardly extending ridges for being engaged by said cantilever latching members to prevent rotation between said adapter and said needle sheath to permit said syringe barrel to be disconnected and removed from said adapter without unlocking said adapter from said needle sheath.

39. The kit according to claim 34 wherein said kit further comprises a receptacle for receiving said syringe barrel, said syringe needle, said needle sheath and said adapter, and packaging means for enclosing said receptacle and said syringe barrel, said syringe needle, said needle sheath and said adapter and providing a barrier to prevent the passage of contaminants therethrough.

40. Apparatus for preventing accidental needle sticks from a used hypodermic needle, comprising:
  a needle sheath having a closed bottom and an outwardly flared top portion providing a first camming surface and an upwardly extending circular groove; and
  an adapter including a first end providing a first luer connector for being threadedly connected to a syringe barrel upon relative rotation between said adapter and the syringe barrel, and said adapter including a second end opposite said first end and providing a second luer connector for being connected to a needle hub from which the hypodermic needle extends, and said adapter provided with a pair of opposed and spaced apart cantilever latching members including outer portions providing second camming surfaces and a pair of hook members;
  said second camming surfaces for engaging said first camming surfaces as said hypodermic needle is being inserted into said needle sheath after use and for camming and flexing said outer portions of said latching members outwardly to permit said lower portions of said latching members to pass over said upper portion of said needle sheath and upon said outer portions of said latching members passing over said upper portion of said needle sheath said lower portions of said latching members flexing inwardly to cause said hook members to reside in said circular groove to lock said adapter to said needle sheath and to entrap said hypodermic needle between said adapter and said needle sheath; and said upper portion of said needle sheath provided with a pair of opposed and outwardly extending ridges and said lower portions of said latching members for engaging said ridges to prevent rotation between said adapter and said needle sheath to permit the syringe barrel to be rotated with respect to said adapter and removed therefrom without unlocking said adapter from said needle sheath.

41. Combination apparatus for use with a syringe barrel and for use with a syringe needle including a needle hub and a hypodermic needle, said apparatus for preventing accidental needle sticks from the hypodermic needle after use, comprising:

a needle sheath;

an adapter for being removably connected to the syringe barrel and for being connected to the needle hub, said adapter for providing liquid communication between the syringe barrel and the syringe needle, said needle sheath and said adapter provided with cooperative means for fastening said adapter to said needle sheath to entrap the hypodermic needle in said needle sheath between said adapter and said needle sheath, and said cooperative means for preventing relative movement between said adapter and said needle sheath to permit said syringe barrel to be removed from said adapter without unfastening said adapter from said needle sheath.

42. Apparatus for preventing hypodermic needle sticks comprising combination syringe needle and cantilever latching means, said syringe needle including a needle hub and a hypodermic needle, said combination syringe needle and cantilever latching means for being connected removably to a syringe barrel to place said needle hub and hypodermic needle in fluid communication with the syringe barrel and upon said hypodermic needle being inserted into a needle sheath, said combination syringe needle and cantilever latching means for latching to the needle sheath sufficiently tightly and non-rotatably to entrap said hypodermic needle in the needle sheath and to permit the syringe barrel to be disconnected form said combination syringe needle and cantilever latching means without disconnecting said combination syringe needle and cantilever latching means from the needle sheath.

43. The apparatus according to claim 42 wherein said combination syringe needle and cantilever latching means comprise a pair of diametrically opposed and radially outwardly extending external resilient cantilever latching members formed integrally with said syringe needle.

44. The apparatus according to claim 43 wherein said needle hub includes upper and lower portions, and wherein said cantilever latching members include respective top end portions formed integrally with said upper portion of said needle hub and respective bottom end portions extending along and spaced from said lower portion of said needle hub.

45. The apparatus according to claim 44 wherein said second end portions of said pair of cantilever latching members include inwardly extending hook portions.

46. The apparatus according to claim 42 wherein said combination syringe needle and cantilever latching means comprise a needle hub and hypodermic needle and an adapter provided with a pair of diametrically opposed and radially outwardly extending external resilient cantilever latching members for latching to the needle sheath, said needle hub providing a first luer connector and said adapter including a first end portion providing a second luer connector for being connected removably to a third luer connector provided on a syringe barrel and a second end portion providing a third luer connector for being connected to said first luer connector, said adapter provided with an internal passageway for placing the syringe barrel and said needle hub and hypodermic needle in fluid communication.

47. The apparatus according to claim 46 wherein said adapter includes a body having a central axis and wherein said internal passageway extends axially and centrally through said body, said body including a first cylindrical end portion having a first outer diameter and an opposed second cylindrical end portion having a second diameter larger than said first diameter, said first cylindrical end portion providing said second luer connector and said second cylindrical providing said third luer connector, said body including a pair of external diametrically opposed longitudinally extending resilient cantilever latching members spaced from each other and extending generally parallel to said central axis, said latching members including inner end portions and outer end portions, said inner end portions of said latching members formed integrally with said first cylindrical portion of said body and extending outwardly therefrom and said outer end portions of said latching members provided with inwardly extending hook portions.

48. Combination apparatus for use with a syringe barrel and for preventing accidental needle sticks, comprising:

a needle sheath; and combination syringe needle and cantilever latching means being connected removably to the syringe barrel to place said syringe needle and the syringe barrel in fluid communication, said combination syringe needle and cantilever latching means including a needle hub and a hypodermic needle extending outwardly from said needle hub, upon said hypodermic needle being inserted into said needle sheath said combination syringe needle and cantilever latching means for latching to said needle sheath sufficiently tightly and non-rotatably to entrap said hypodermic needle within said needle sheath and to permit the syringe barrel to be disconnected from said combination syringe needle and cantilever latching means without unlatching said combination syringe needle and cantilever latching means from said needle sheath.

49. The apparatus according to claim 48 wherein said needle sheath includes an enlarged open top portion and a closed bottom portion, wherein said top portion provides an inclined camming surface and includes an underside provided with an upwardly extending circular groove.

50. The apparatus according to claim 49 wherein said combination syringe needle and cantilever latching means include a pair of diametrically opposed and radially outwardly extending external resilient cantilever latching members including upper portions formed integrally with said needle hub and lower portions extending along a portion of and spaced from said hypodermic needle and including inwardly and upwardly extending hook portions for being hooked into said circular groove to latch said cantilever latching members and thereby said combination syringe needle and cantilever latching means to said needle sheath.

51. A kit comprising:

a syringe barrel including a first luer connector;

combination syringe needle and cantilever latching means including a second luer connector for being connected to said first luer connector to place said syringe barrel and said combination syringe needle and cantilever latching means in fluid communication;

a needle sheath provided with a pair of diametrically opposed and outwardly extending external ridges; and said combination syringe needle and cantilever latching means including a needle hub, a hypodermic needle and a pair of external and generally diametrically opposed resilient cantilever latching members formed integrally with said needle hub, said cantilever latching members for latching to said needle sheath sufficiently tightly to entrap said hypodermic needle within said needle sheath upon said hypodermic needle being inserted therein after use and for engaging said external ridges to prevent rotation between said combination syringe needle and cantilever latching means and said needle sheath to permit said syringe barrel to be rotated, disconnected and removed from said combination syringe needle and cantilever latching means without unlatching and removing said combination syringe needle and cantilever latching means from said needle sheath.

* * * * *